(12) United States Patent
Maruyama

(10) Patent No.: US 8,303,868 B2
(45) Date of Patent: Nov. 6, 2012

(54) WET GRANULATION TABLETING METHOD USING AQUEOUS DISPERSION OF LOW-SUBSTITUTED HYDROXYPROPYL CELLULOSE

(75) Inventor: Naosuke Maruyama, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 152 days.

(21) Appl. No.: 12/693,226

(22) Filed: Jan. 25, 2010

(65) Prior Publication Data

US 2010/0187706 A1 Jul. 29, 2010

(30) Foreign Application Priority Data

Jan. 26, 2009 (JP) .................................. 2009-014082

(51) Int. Cl.
*B29C 43/02* (2006.01)
(52) U.S. Cl. ......................... 264/115; 264/109; 264/123
(58) Field of Classification Search ........................ None
See application file for complete search history.

(56) References Cited

U.S. PATENT DOCUMENTS

| | | | |
|---|---|---|---|
| 3,852,421 A | | 12/1974 | Koyanagi et al. |
| 4,091,205 A | | 5/1978 | Onda et al. |
| 5,855,914 A | * | 1/1999 | Koyama et al. ............... 424/494 |
| 6,245,351 B1 | * | 6/2001 | Nara et al. ..................... 424/461 |
| 6,559,134 B2 | | 5/2003 | Tanno et al. |
| 2006/0204572 A1 | * | 9/2006 | Higuchi et al. ............... 424/464 |
| 2007/0248681 A1 | * | 10/2007 | Hoshino et al. .............. 424/494 |

FOREIGN PATENT DOCUMENTS

| | | |
|---|---|---|
| EP | 1 192 942 A2 | 3/2002 |
| EP | 1 967 211 A1 | 9/2008 |
| JP | 5271054 A | 10/1993 |
| JP | 9048726 A | 2/1997 |
| JP | 9071532 A | 3/1997 |
| JP | 11043429 A | 2/1999 |
| JP | 2000-103731 A | 4/2000 |
| JP | 2001-328948 | 11/2001 |
| JP | 2002-104956 A | 4/2002 |
| JP | 2002-308760 | 10/2002 |
| JP | 3408398 | 5/2003 |
| JP | 2006-282551 A | 10/2006 |
| JP | 2007-137802 A | 6/2007 |
| WO | WO 99/59544 A2 | 11/1999 |
| WO | WO 2008/148733 A2 | 12/2008 |
| WO | WO 2009/022670 A1 | 2/2009 |
| WO | WO 2009/113703 A2 | 9/2009 |

OTHER PUBLICATIONS

Kawashima, Y. et al., *Preparation of Prolonged-Release Matrix Tablet of Acetaminophen With Pulverized Low-Substituted Hydroxypropylcellulose Via Wet Granulation*, International Journal of Pharmaceutics, 99, (1993), pp. 229-238.

Sugimori, K. et al., *Effects of Granulation Method and Drug Dissolved in Binder Solution on Compressibility of Granules*, Chem. Pharm. Bull. 38 (1), (1990), pp. 188-192.

European Search Report for Application No. EP 10 15 1595 dated Dec. 16, 2010.

* cited by examiner

*Primary Examiner* — Mary F Theisen
(74) *Attorney, Agent, or Firm* — Alston & Bird LLP

(57) ABSTRACT

Provided is a method for preparing a tablet having high tablet hardness and an excellent disintegration property even if low-substituted hydroxypropyl cellulose is added in a relatively small amount. More specifically, provided is a method for preparing a tablet comprising steps of granulating while spraying an aqueous dispersion of low-substituted hydroxypropyl cellulose having a degree of hydroxypropoxyl group substitution ranging from 5 to 16% by weight to a tablet-forming composition and tableting the resulting granules.

4 Claims, 2 Drawing Sheets

WET GRANULATION TABLETING METHOD USING AQUEOUS DISPERSION OF LOW-SUBSTITUTED HYDROXYPROPYL CELLULOSE

CROSS-REFERENCE TO RELATED APPLICATIONS

This application is based on and claims priority to Japanese Patent Application No. 2009-014082, filed Jan. 26, 2009, which is incorporated by reference herein in its entirety.

FIELD OF THE INVENTION

The present invention relates to a method for preparing a tablet by using low-substituted hydroxypropyl cellulose to be added to give, when preparations are manufactured in the fields of medicine, food, etc., thereto a disintegration property or a binding property. In particular, the invention relates to a wet granulation tableting method.

BACKGROUND

Solid preparations in the fields of medicine, food, etc., have such problems that preparations composed only of a principal ingredient sometimes cannot exhibit an effect of the ingredient fully because they do not disintegrate sufficiently even when they are administered; and solid preparations in the form of tablets or granules cannot retain their shape because of a poor binding property. In such a case, addition of a disintegrant such as low-substituted hydroxypropyl cellulose, carboxymethylcellulose calcium salt, crosslinked carboxymethylcellulose sodium, cross-linked polyvinylpyrrolidone, or carboxymethyl starch can improve the disintegration property. On the other hand, addition of crystalline cellulose or a water-soluble binder can improve the binding property. Low-substituted hydroxypropyl cellulose is known as a unique additive having both the disintegration property and the binding property. In addition to this advantage, the low-substituted hydroxypropyl cellulose is nonionic so that it is free from deterioration due to the reaction with an ionic drug.

Japanese Patent Application Examined Publication Nos. 48-38858/1973 and 57-53100/1982 describe that low-substituted hydroxypropyl cellulose can be used as an additive to pharmaceuticals.

Low-substituted hydroxypropyl cellulose can be prepared by reacting alkali cellulose with propylene oxide as described in Japanese Patent No. 3408398.

Examples of the dosage form in the fields of medicine, food, etc., include tablets, capsules and granules. Of these, the tablets are most popular from the standpoint of convenience and administration ease.

Examples of the method for preparing a tablet may include a dry direct tableting method in which after dry mixing of a drug with a binder, a disintegrant, an extender, a lubricant, and the like, the resulting mixture is tableted; and a wet granulation tableting method in which after a drug, a binder, a disintegrant, an extender, and the like are granulated using water or an aqueous solution of a binder and the resulting granule is dried, powders thus obtained and a lubricant are mixed, followed by tableting.

In the wet granulation tableting method, it is the common practice to place a drug, a binder, a disintegrant, an extender and the like in powder form in a fluidized bed granulator or high speed agitation granulator, and granulate the mixture by using water, ethanol or the like. It is, however, known that when tablets having predetermined tablet hardness cannot be obtained or tableting problems such as capping, lamination and sticking occur, granulating while spraying or adding an aqueous solution of a water-soluble binder such as hydroxypropyl cellulose, polyvinylpyrrolidone, or hydroxypropylmethyl cellulose is effective for achieving high tablet hardness. However, the tablet obtained in such a manner has undesirably a reduced disintegration property because of the use of a water-soluble binder.

In recent years, there has been a demand for the development of rapidly disintegrating oral tablets which elderly or infant patients having an insufficient ability to swallow can easily take without water. Preparation technologies of such tablets are described in the following known literatures.

Japanese Patent Application Unexamined Publication No. 9-48726/1997 discloses a method of forming a drug into a tablet under a humidified condition and then drying it. As a base material for them, sugar, sugar alcohol and water-soluble polymer are exemplified. Japanese Patent Application Unexamined Publication No. 5-271054/1993 discloses a method for preparing a rapidly disintegrating oral tablet containing a drug component and sugar. However, these technologies have such problems that they are very cumbersome, they require special equipment, and tablets thus obtained are likely to cause wear losses or cracks during shipping because they are low in strength.

The following are known literatures on rapidly disintegrating oral tablets using low-substituted cellulose ether.

Japanese Patent Application Unexamined Publication No. 9-71532/1997 discloses rapidly disintegrating oral tablets containing microcrystalline cellulose and low-substituted hydroxypropyl cellulose at a certain ratio. This invention relates to a mixture of low substituted hydroxypropyl cellulose and microcrystalline cellulose, but it requires addition of large amounts of additives and the tablets thus obtained do not have a satisfactory disintegration property.

Japanese Patent Application Unexamined Publication No. 11-43429/1999 describes use of low-substituted hydroxypropyl cellulose having a degree of hydroxypropoxyl group substitution ranging from 7.0 to 9.9% by weight for preparing rapidly disintegrating oral tablets. Similarly, Japanese Patent Application Unexamined Publication No. 2000-103731 describes use of low-substituted hydroxypropyl cellulose having a degree of hydroxypropoxyl group substitution ranging from 5.0 to 7.0% by weight for the same purpose. Since a fibrous condition derived from raw material pulp becomes severer with a decrease in the degree of hydroxypropoxyl group substitution, when the tablets thus obtained disintegrate in the oral cavity, they leave an unpleasant texture to recipients as if they eat paper.

Japanese Patent Application Unexamined Publication No. 2001-328948 describes rapidly disintegrating oral tablets composed of low-substituted hydroxypropyl cellulose and sugar alcohol. However, the method disclosed herein does not succeed in providing a tablet having high tablet hardness.

Japanese Patent Application Unexamined Publication No. 2002-104956 describes a base material for dry direct tableting obtained by impregnating low-substituted hydroxypropyl cellulose with sugar or sugar alcohol and then drying the resulting mixture. It is not obtained by granulating using an aqueous dispersion of low-substituted hydroxypropyl cellulose.

Japanese Patent Application Unexamined Publication No. 2002-308760 describes sugar coated with aluminometasilicate. However, it is not obtained by granulating using an aqueous dispersion of low-substituted hydroxypropyl cellulose.

Japanese Patent Application Unexamined Publication No. 2006-282551 describes use of α-starch or the like as a binder soluble or swellable in water, together with delta type mannitol. However, it does not include description of low-substituted hydroxypropyl cellulose.

SUMMARY OF THE INVENTION

With the foregoing in view, the present invention has been made. An object of the invention is to provide a method for preparing a tablet having high tablet hardness and at the same time having an excellent disintegration property by wet granulation tableting even when low-substituted hydroxypropyl cellulose is added in a relatively small amount.

The present inventors have carried out an intensive investigation in order to achieve the above-described object. As a result, it has been found that a tablet having high tablet hardness and at the same time having an excellent disintegration property can be obtained by tableting granules obtained by using an aqueous dispersion of low-substituted hydroxypropyl cellulose in wet granulation tableting, leading to the completion of the invention.

The invention provides a method for preparing a tablet having both high tablet hardness and an excellent disintegration property by tableting granules obtained using an aqueous dispersion of low-substituted hydroxypropyl cellulose in wet granulation tableting.

More specifically, the preparation method comprises at least a step of granulating while spraying, to a tablet-forming composition, an aqueous dispersion of low-substituted hydroxypropyl cellulose having a degree of hydroxypropoxyl group substitution ranging from 5 to 16% by weight and a step of tableting the resulting granules into a tablet.

Tablets having both high tablet hardness and an excellent disintegration property can be obtained by tableting granules whose surfaces have been modified with spray of an aqueous dispersion of low-substituted hydroxypropyl cellulose in wet granulation tableting. The invention enables to prepare tablets having excellent disintegratabillity in an oral cavity and having a strength necessary and sufficient during preparation or shipping of the tablets. Accordingly, the tablets suited for orally administering various drugs in the fields of medicine, food, etc., can be provided and taken by recipients very smoothly.

DETAILED DESCRIPTION OF THE PREFERRED EMBODIMENTS

Figure 1:
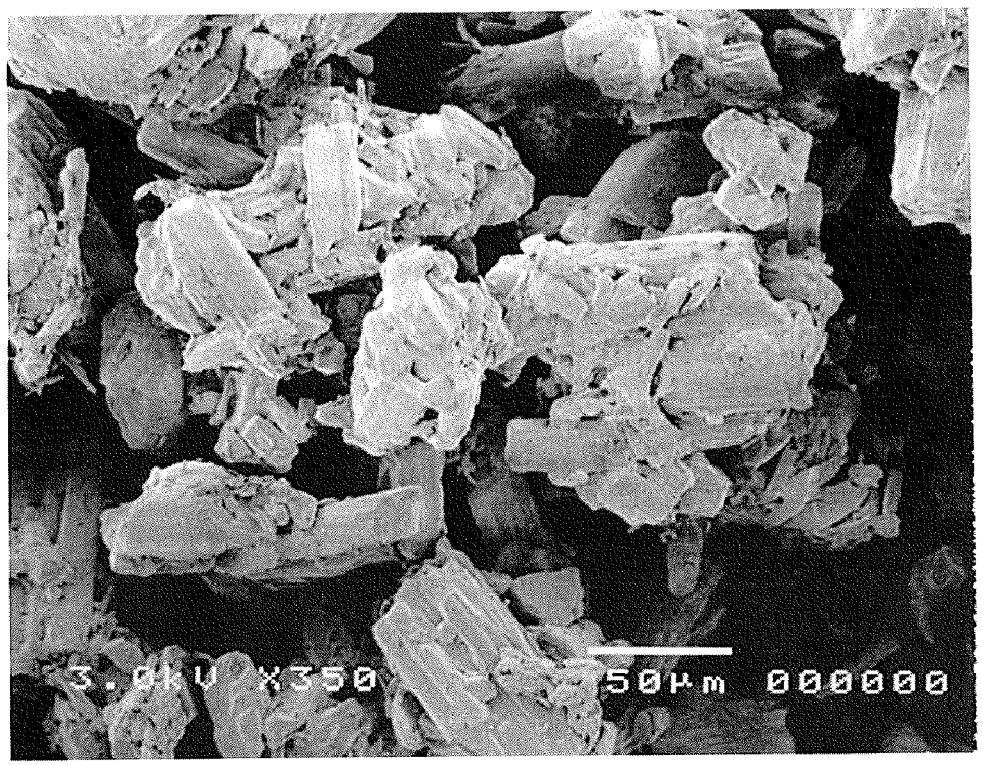
FIG. 1 is an electron micrograph of granulates obtained in Example 1.

Low-substituted hydroxypropyl cellulose usable in the invention is a water-insoluble polymer. It has a property of absorbing water and swelling therewith. It has a basic skeleton of cellulose with a small amount of hydroxypropoxyl groups introduced therein. The degree of hydroxypropoxyl group substitution is from 5 to 16% by weight as described in the Japanese Pharmacopoeia and this range is also preferred in the invention. When the degree of hydroxypropoxyl group substitution is less than 5% by weight, a swelling property after water absorption is low and the resulting tablets may not show the intended disintegration property. In addition, they may have a reduced binding property. When the degree of hydroxypropoxyl group substitution is more than 16% by weight, the swelling property and the binding property improve, but water solubility increases. As a result, the tablets thus obtained may not show the intended disintegration property and require a long disintegration time. The degree of hydroxypropoxyl group substitution is measured based on the Japanese Pharmacopoeia.

Low-substituted hydroxypropyl cellulose usable in the invention has an average particle size of preferably from about 5 to 100 μm, more preferably from about 10 to 60 μm. When it has an average particle size less than 5 μm, the resulting tablets may have a deteriorated disintegration property due to deterioration in water absorption and swelling properties. When it has an average particle size exceeding 100 μm, the resulting tablets may have a deteriorated binding property due to a decrease in specific surface area. It is to be noted that the term "average particle size" as used herein means a volume particle size and it is measured in accordance with the powder particle size analysis using laser diffraction. It can be measured, for example, by using "HELOS&RODOS" (product of Japan Laser).

The content of the low-substituted hydroxypropyl cellulose in the preparation may be preferably from 1 to 20% by weight, more preferably from 2 to 10% by weight. When the content is less than 1% by weight, tablets having the intended tablet hardness and disintegration property may not be obtained. When the content is more than 20% by weight, marked improvement in the tablet-forming property and the disintegration property may not be observed and the diameter of the resulting tablets may increase.

The concentration of the low-substituted hydroxypropyl cellulose in the aqueous dispersion may be preferably from 1 to 15% by weight, more preferably from 5 to 10% by weight. When the concentration is less than 1% by weight, it may take a long time to spray a predetermined amount so that the productivity may be deteriorated. When the concentration is more than 15% by weight, the aqueous dispersion may not be fed because its viscosity becomes too high.

A method for preparing the aqueous dispersion of the low-substituted hydroxypropyl cellulose is very simple and convenient. It may be prepared by pouring the low-substituted hydroxypropyl cellulose in a predetermined amount of water or on the contrary, by pouring water in the low-substituted hydroxypropyl cellulose. Since the low-substituted hydroxypropyl cellulose is insoluble in water, it can be dispersed speedily. Only mixing for several minutes with a conventional stirrer may be sufficient. Water-soluble hydroxypropyl cellulose gelates when it is poured in water, but an aqueous dispersion of the low-substituted hydroxypropyl cellulose of the invention can be prepared easily. The dispersion is preferably stirred gently when it is being fed for granulation in order to prevent precipitation.

In wet granulation according to the invention, a fluidized bed granulator capable of simultaneously spraying and drying and readily forming a uniform covering layer may be preferred. Since an agitation granulator is not equipped with a drying apparatus, there is a possibility that the granules agglomerate due to an excess amount of water when a predetermined amount of aqueous dispersion of low-substituted hydroxypropyl cellulose is added.

The tablet-forming composition may preferably comprise at least a drug as well as sugar or sugar alcohol in powder form. In the fluidized bed granulation, it is possible to place the tablet-forming composition such as a drug and a sugar or sugar alcohol in powder form and then carry out granulation in a conventional manner. It is only necessary to spray an aqueous dispersion of low-substituted hydroxypropyl cellulose instead of using an aqueous solution of a water-soluble binder as a binder fluid. The fluidized bed granulation therefore does not require use of a special apparatus.

The average particle size of the granules differs depending on the granulation conditions, but it may be preferably from 100 to 500 μm. When the average particle size is less than 100 μm, the granules may stick to a tableting machine due to low fluidity. When the average particle size is more than 500 μm, the resulting tablets may vary greatly in weight due to a deterioration in the filling property of the granules in a die cavity. The average particle size of the granules can be measured by the analytical sieving method described in General Test Methods of the Japanese Pharmacopoeia.

The granules thus obtained do not need further drying when drying is performed using a fluidized bed granulator capable of simultaneously spraying and drying. When drying is not performed or a granulator incapable of drying is used, on the other hand, the granules can be dried in a known manner, for example, at 40 to 80° C. by using a fluidized-bed dryer or a tray dyer.

After the granules are mixed with a lubricant, the resulting mixture can be tableted in an ordinary rotary type continuous tableting machine. Although the size of the tablet can be selected freely, the tablet may have preferably a diameter of from about 6 to 12 mm and a weight of from 70 to 700 mg/tablet. The tablet having a diameter of less than 6 mm may not be handled easily, while the tablet having a diameter of more than 12 mm may be difficult to be swallowed.

A tableting pressure may be preferably from 10 to 100 mPa. When the tableting pressure is less than 10 mPa, the resulting tablets may not have the intended tablet hardness. When the compression pressure is more than 100 mPa, tableting problems such as capping may occur.

The drug to be used in the invention may include, but not limited to, drugs for the central nervous system, drugs for the circulatory system, drugs for the respiratory system, drugs for the digestive system, antibiotics and chemotherapeutic agents, drugs for the metabolic system, and vitamin preparations.

Examples of the drugs for the central nervous system may include diazepam, idebenone, aspirin, ibuprofen, paracetamol, naproxen, piroxicam, diclofenac, indomethacin, sulindac, lorazepam, nitrazepam, phenyloin, acetaminophen, ethenzamide and ketoprofen.

Examples of the drugs for the circulatory system may include molsidomine, vinpocetine, propranolol, methyldopa, dipyridamole, furosemide, triamterene, nifedipine, atenolol, spironolactone, metoprolol, pindolol, captopril and isosorbide nitrate.

Examples of the drugs for the respiratory system may include amlexanox, dextromethorphan, theophylline, pseudoephedrine, salbutamol and guaifenesin.

Examples of the drugs for the digestive system may include benzimidazole-based drugs having an antiulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole, cimetidine, ranitidine, pancreatin, bisacodyl and 5-aminosalicylic acid.

Examples of the antibiotics and chemotherapeutic agents may include cephalexin, cefaclor, cefradine, amoxicillin, pivampicillin, bacampicillin, dicloxacillin, erythromycin, erythromycin stearate, lincomycin, doxycycline and trimethoprim/sulfamethoxazole.

Examples of the drugs for the metabolic system may include serrapeptase, lysozyme hydrochloride, adenosine triphosphate, glibenclamide and potassium chloride.

Examples of the vitamin drugs may include vitamin B1, vitamin B2, vitamin B6 and vitamin C.

As an excipient, use of sugar or sugar alcohol such as erythritol, mannitol, sorbitol, lactose or sucrose which is excellent in a disintegration property may be preferred. Its content in the preparation may be preferably from 10 to 95% by weight, more preferably from 20 to 80% by weight.

In preparing the tablets of the invention, an additive ordinary used for solid preparations may be added in a normal amount. Examples of such an additive may include a disintegrant, a binder, an extender, a lubricant, a taste corrigent and a flavor.

Examples of the disintegrant may include low-substituted hydroxypropyl cellulose, corn starch, potato starch, partially α starch, carboxymethyl starch sodium, carmellose, croscarmellose sodium, crystalline cellulose and crospovidone.

Examples of the binder may include hydroxypropyl cellulose, polyvinylpyrrolidone and hydroxypropylmethyl cellulose.

Examples of the extender may include erythritol, mannitol, sorbitol, lactose, sucrose, calcium phosphate and calcium sulfate.

Examples of the taste corrigent may include citric acid, tartaric acid and malic acid.

Examples of the flavor may include menthol, peppermint oil and vanillin.

Examples of the lubricant may include magnesium stearate and sucrose fatty acid ester.

According to the invention, an aqueous dispersion of a water-insoluble low-substituted hydroxypropyl cellulose is sprayed to the surface of the granule to cover the surface and thereby modify the surface. It makes possible to satisfy both high tablet hardness and a fast disintegration property while suppressing tableting problems even when the low-substituted hydroxypropyl cellulose is added in a relatively small amount. Both high tablet hardness and a fast disintegration property can be satisfied presumably because by spraying and covering the granule with an aqueous dispersion of low-substituted hydroxypropyl cellulose, the surface of the granule is covered with the low-substituted hydroxypropyl cellulose and due to an increase in contact points of the low-substituted hydroxypropyl cellulose at the time of compression molding, a firm hydrogen bond is formed, leading to improvement of a binding property; and presumably because the low-substituted hydroxypropyl cellulose has a property of quickly absorbing water and swelling therewith so that the compression molded product obtained in the above manner disintegrates rapidly.

EXAMPLES

The invention will hereinafter be described specifically by Examples and Comparative Examples. It should not be construed that the invention is limited to or by them.

Example 1

D-mannitol (285 g) was placed in a fluidized bed granulator. Granulation was performed while spraying thereto 214 g of a 7% by weight aqueous dispersion of low-substituted hydroxypropyl cellulose (degree of hydroxypropoxyl group substitution: 14% by weight, average particle size: 35 μm) at an intake gas temperature of 60° C., an exhaust gas temperature of 27 to 30° C., an air flow of 50 m³/hr, a spray rate of 12 g/min and a spray air pressure of 150 kPa. An electron micrograph of the granules thus obtained is shown in FIG. 1.

After magnesium stearate was added as a lubricant to the resulting granules, the resulting mixture was tableted under the following conditions.

Composition

| | |
|---|---|
| D-mannitol | 95 parts by weight |
| Low-substituted hydroxypropyl cellulose (degree of hydroxypropoxyl group substitution: 14% by weight) | 5 parts by weight |
| Magnesium stearate | 1 part by weight |

Tableting machine: rotary tableting machine (product of Kikusui Seisakusho)
Tablet size: diameter: 8 mm, curvature radius: 10 mm, tablet weight: 200 mg
Tableting pressure: main pressure: 0.5 t, 0.75 t, 1.0 t, pre-pressure: 0.3 t
Tableting rate: 20 rpm Evaluation results of the tablets thus obtained (tablet hardness, tablet friability in the tablet friability test of the Japanese Pharmacopoeia, disintegration time (test fluid: water) in the disintegration test of the Japanese Pharmacopoeia) are shown in Table 1. The tablet hardness can be determined from the maximum breaking strength at which the tablet is broken as a result of application of a load at a constant rate in a diameter direction of the tablet. Since the tablet hardness sometimes varies, depending on the load application rate, measurement is performed at a rate of 1 mm/sec.

Example 2

In the same manner as in Example 1 except that the low-substituted hydroxypropyl cellulose used in Example 1 was replaced with low-substituted hydroxypropyl cellulose (degree of hydroxypropoxyl group substitution: 11% by weight, average particle size: 33 μm), tablets were obtained.

The tablets thus obtained were evaluated in the same manner as in Example 1 and the results are shown in Table 1.

Comparative Example 1

Granulation was performed by using the same low-substituted hydroxypropyl cellulose as that used in Example 1 and using water instead of the aqueous dispersion.

Figure 2:
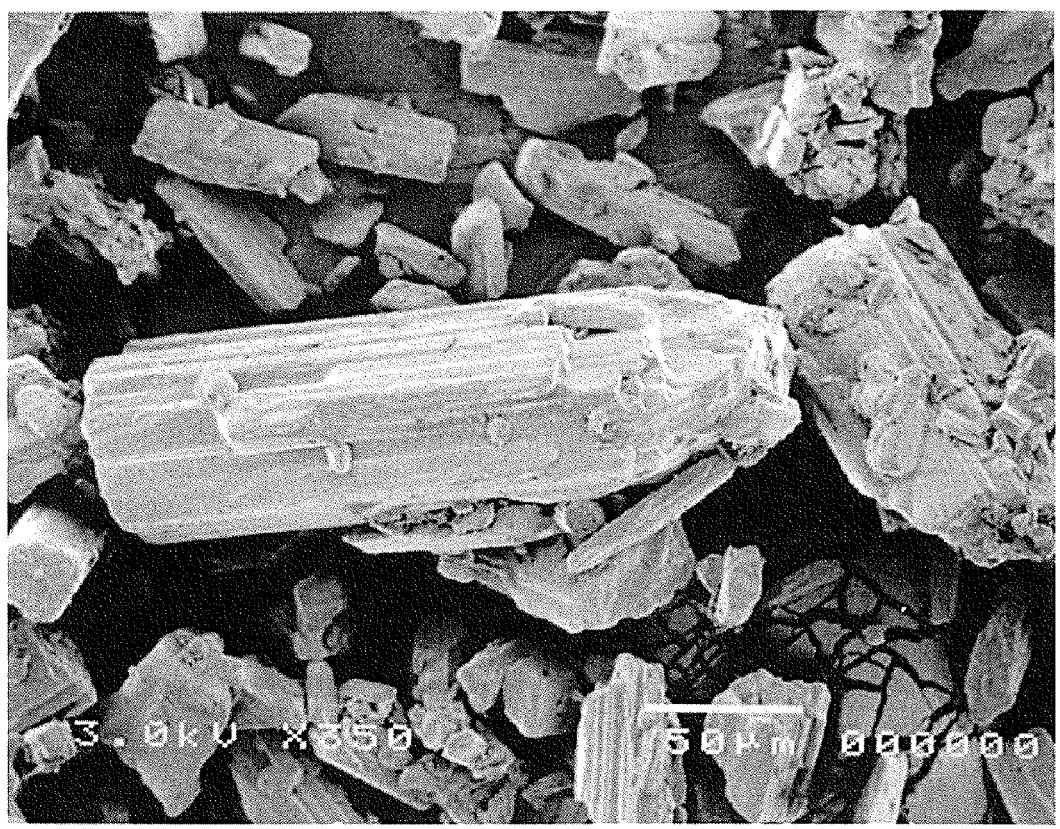
FIG. 2 is an electron micrograph of granulates obtained in Comparative Example 1.

D-mannitol (285 g) and 15 g of low-substituted hydroxypropyl cellulose (degree of hydroxypropoxyl group substitution: 14% by weight, average particle size: 35 μm) were placed in a fluidized bed granulator. Granulation was carried out while spraying 200 g of purified water thereto at an intake gas temperature of 60° C., an exhaust gas temperature of 27 to 30° C., an air flow of 50 m$^3$/hr, a spray rate of 12 g/min and a spray air pressure of 150 kPa. An electron micrograph of the granules thus obtained is shown in FIG. 2.

After magnesium stearate was added as a lubricant to the resulting granules, the resulting mixture was tableted under the following conditions.

Composition

| | |
|---|---|
| D-mannitol | 95 parts by weight |
| Low-substituted hydroxypropyl cellulose (degree of hydroxypropoxyl group substitution: 14% by weight) | 5 parts by weight |
| Magnesium stearate | 1 part by weight |

Tablet press: rotary tablet press (product of Kikusui Seisakusho)
Tablet size: diameter: 8 mm, curvature radius: 10 mm, tablet weight: 200 mg
Tableting pressure: main pressure: 0.5 t, 0.75 t, 1.0 t, Pre-pressure: 0.3 t
Tableting rate: 20 rpm The tablets thus obtained were evaluated in the same manner as in Example 1 and the results are shown in Table 1.

Comparative Example 2

Granulation was performed using the same low-substituted hydroxypropyl cellulose as that used in Example 2 and using water instead of the aqueous dispersion. More specifically, tablets were obtained in the same manner as in Comparative Example 1 except that the low-substituted hydroxypropyl cellulose used in Comparative Example 1 was replaced with low-substituted hydroxypropyl cellulose (degree of hydroxypropoxyl group substitution: 11% by weight, average particle size: 33 μm).

The tablets thus obtained were evaluated in the same manner as in Example 1 and the results are shown in Table 1.

Comparative Example 3

In the same manner as in Example 1 except that 214 g of the 7% by weight aqueous dispersion of low-substituted hydroxypropyl cellulose in Example 1 was replaced by 214 g of a 7% by weight aqueous solution of hydroxypropyl cellulose HPC-L (degree of hydroxypropoxyl group substitution: 62% by weight), tablets were obtained.

The tablets thus obtained were evaluated in the same manner as in Example 1 and the results are shown in Table 1.

Comparative Example 4

In the same manner as in Example 1 except that 214 g of the 7% by weight aqueous dispersion of low-substituted hydroxypropyl cellulose in Example 1 was replaced by 214 g of a 7% by weight aqueous dispersion of microcrystalline cellulose "Ceolus PH-101", tablets were obtained.

The tablets thus obtained were evaluated in the same manner as in Example 1 and the results are shown in Table 1.

The tablets obtained in Examples 1 and 2 in which granulation was performed using an aqueous dispersion of a low-substituted hydroxypropyl cellulose exhibited high tablet hardness, low friability and an excellent disintegration property. On the other hand, the tablets obtained in Comparative Examples 1 and 2 had lower tablet hardness and higher friability than those obtained in Examples.

Such results occur presumably because as can be observed from the electron micrograph of FIG. 1, covering the crystal surface of D-mannitol with low-substituted hydroxypropyl cellulose in Example 1 using the aqueous dispersion increased contact points of the low-substituted hydroxypropyl cellulose at the time of compression molding, whereby a firm hydrogen bond was formed, leading to improvement of a binding property; and presumably because the low-substituted hydroxypropyl cellulose has a property of quickly absorbing water and swelling therewith so that the tablets disintegrated rapidly. On the other hand, when the aqueous dispersion was not used, the crystal surface of D-mannitol was not covered with the low-substituted hydroxypropyl cellulose as is apparent from the electron micrograph of FIG. 2, leading to deterioration in molding property.

The tablets obtained in Comparative Example 3 showed higher tablet hardness than those obtained in Examples, but they needed a longer disintegration time. This is presumed to occur because in spite of improvement in a binding property due to the high degree of hydroxypropoxyl group substitution, the hydroxypropyl cellulose, which is soluble in water, formed a hydrated gel layer of the hydroxypropyl cellulose at the time of disintegration, which disrupted introduction of water into the tablets and prolonged a disintegration time.

In Comparative Example 4, granulation was performed using an aqueous dispersion of microcrystalline cellulose, but the tablets obtained in Comparative Example 4 showed lower tablet hardness, higher friability, and longer disintegration time than those obtained in Examples.

TABLE 1

|  |  | Example 1 | Example 2 | Comp.Ex.1 | Comp.Ex.2 | Comp.Ex.3 | Comp.Ex.4 |
|---|---|---|---|---|---|---|---|
| liquid for spraying additive |  | aqueous dispersion low-substituted hydroxypropyl cellulose | aqueous dispersion low-substituted hydroxypropyl cellulose | water low-substituted hydroxypropyl cellulose | water low-substituted hydroxypropyl cellulose | aqueous solution hydroxypropyl cellulose | aqueous dispersion microcrystalline cellulose |
| degree of hydroxypropoxyl group substitution (% by weight) |  | 14 | 11 | 14 | 11 | 62 | — |
| evaluation | tabletting pressure |  |  |  |  |  |  |
| tablet hardness (kgf) | 0.50 t | 2.8 | 2.5 | 1.9 | 1.7 | 6.3 | 2.0 |
|  | 0.75 t | 5.6 | 3.5 | 3.2 | 2.8 | 8.9 | 3.7 |
|  | 1.00 t | 7.2 | 5.7 | 4.8 | 3.6 | 11.3 | 3.8 |
| tablet friability (%) | 0.50 t | 0.6 | 0.8 | 1.2 | 1.4 | 0.3 | 1.7 |
|  | 0.75 t | 0.4 | 0.5 | 0.7 | 0.7 | 0.1 | 0.6 |
|  | 1.00 t | 0.2 | 0.3 | 0.4 | 0.3 | 0.1 | 0.9 |
| tablet disintegration time (seconds) | 0.50 t | 13 | 10 | 11 | 10 | 660 | 15 |
|  | 0.75 t | 16 | 12 | 12 | 11 | 696 | 37 |
|  | 1.00 t | 18 | 15 | 13 | 11 | 702 | 78 |

Example 3

Acetaminophen (120 g) and 150 g of 200 mesh lactose were placed in a fluidized bed granulator. Granulation was performed while spraying thereto 428 g of 7% by weight aqueous dispersion of low-substituted hydroxypropyl cellulose (degree of hydroxypropoxyl group substitution: 14% by weight, average particle size: 35 μm) at an intake gas temperature of 60° C., an exhaust gas temperature of 27 to 28° C., an air flow of 50 m$^3$/hr, a spray rate of 15 g/min, and a spray air pressure of 150 kPa.

After magnesium stearate was added as a lubricant to the resulting granules, the resulting mixture was tableted under the following conditions.

Composition

| | |
|---|---|
| Acetaminophen | 40 parts by weight |
| Lactose | 50 parts by weight |
| Low-substituted hydroxypropyl cellulose (degree of hydroxypropoxyl group substitution: 14% by weight) | 10 parts by weight |
| Magnesium stearate | 0.5 part by weight |

Tablet press: rotary tablet press (product of Kikusui Seisakusho)

Tablet size: diameter: 8 mm, curvature radius: 10 mm, tablet weight: 200 mg

Tabletting pressure: main pressure: 0.5 t, 0.75 t, 1.0 t, Pre-pressure: 0.3 t

Tabletting rate: 20 rpm

Evaluation results of the tablets thus obtained (tablet hardness, tablet friability in the tablet friability test of the Japanese Pharmacopoeia, disintegration time (test fluid: water) in the disintegration test of the Japanese Pharmacopoeia, capping ratio after the friability test) are shown in Table 2. The tablet hardness was measured in the same manner as in Example 1. The capping is a cap-like separating phenomenon of tablet that occurs when or after the tablet is discharged from a tabletting machine. After the friability test was made in accordance with the Japanese Pharmacopoeia, the number of tablets which had caused capping was counted and a capping ratio was calculated based on the following equation.

Capping ratio=[(the number of tablets which caused capping)/(the number of tested tablets)]×100

Comparative Example 5

In the same manner as in Example 3 except that 428 g of the 7% by weight aqueous dispersion of low-substituted hydroxypropyl cellulose was replaced by 428 g of 7% by weight aqueous dispersion of microcrystalline cellulose "Ceolus PH-101", tablets were prepared.

The tablets thus obtained were evaluated in the same manner as in Example 3 and the results are shown in Table 2.

TABLE 2

|  |  | Example 3 | Comparative Example 5 |
|---|---|---|---|
|  |  | liquid for spraying | |
|  |  | aqueous dispersion additive | aqueous dispersion additive |
| evaluation | tabletting pressure | low-substituted hydroxypropyl cellulose | microcrystalline cellulose |
| tablet hardness (kgf) | 0.50 t | 2.2 | 2.0 |
|  | 0.75 t | 3.8 | 3.6 |
|  | 1.00 t | 5.1 | 3.7 |
|  | 1.25 t | 7.1 | 3.3 |
| tablet friability (%) | 0.50 t | 0.7 | 1.2 |
|  | 0.75 t | 0.4 | 0.6 |
|  | 1.00 t | 0.2 | 1.5 |
|  | 1.25 t | 0.2 | 2.7 |
| tablet disintegration time (seconds) | 0.50 t | 17 | 15 |
|  | 0.75 t | 17 | 15 |
|  | 1.00 t | 20 | 24 |
|  | 1.25 t | 20 | 130 |
| capping ratio (%) | 0.50 t | 0 | 0 |
|  | 0.75 t | 0 | 0 |
|  | 1.00 t | 0 | 25 |
|  | 1.25 t | 0 | 85 |

The tablets obtained in Example 3 exhibited high tablet hardness, low friability, and short disintegration time, and caused no tablet problems such as capping. On the other hand, the tablets obtained in Comparative Example 5 showed low tablet hardness, high friability, and long disintegration time and when the tableting pressure was high, they caused capping.

The invention claimed is:

1. A method for preparing a tablet, comprising steps of:
    granulating while spraying an aqueous dispersion of low-substituted hydroxypropyl cellulose having a degree of hydroxypropoxyl group substitution ranging from 5 to 16% by weight to a tablet-forming composition and tableting granules thus obtained.

2. The method for preparing a tablet according to claim 1, wherein said step of granulating comprises granulation in a fluidized bed granulator.

3. The method for preparing a tablet according to claim 1, wherein said tablet-forming composition comprises a drug as well as sugar or sugar alcohol in powder form.

4. The method for preparing a tablet according to claim 2, wherein said tablet-forming composition comprises a drug as well as sugar or sugar alcohol in powder form.

* * * * *

UNITED STATES PATENT AND TRADEMARK OFFICE
CERTIFICATE OF CORRECTION

PATENT NO.       : 8,303,868 B2                                    Page 1 of 1
APPLICATION NO.  : 12/693226
DATED            : November 6, 2012
INVENTOR(S)      : Maruyama It is certified that error appears in the above-identified patent and that said Letters Patent is hereby corrected as shown below:

Column 5,
Line 38, "phenyloin" should read --phenytoin--.

Signed and Sealed this
Second Day of April, 2013

Teresa Stanek Rea
*Acting Director of the United States Patent and Trademark Office*